US009656952B2

(12) United States Patent
Ono et al.

(10) Patent No.: US 9,656,952 B2
(45) Date of Patent: May 23, 2017

(54) REACTION ACCELERATOR AND METHOD OF PRODUCING URETHANE COMPOUND, THIOURETHANE COMPOUND, AMIDE COMPOUND, OR UREA COMPOUND USING SAME

(71) Applicant: SHOWA DENKO K.K., Tokyo (JP)

(72) Inventors: Katsutoshi Ono, Tokyo (JP); Tomomitsu Kato, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 14/906,759

(22) PCT Filed: Jul. 22, 2014

(86) PCT No.: PCT/JP2014/069309
§ 371 (c)(1),
(2) Date: Jan. 21, 2016

(87) PCT Pub. No.: WO2015/012259
PCT Pub. Date: Jan. 29, 2015

(65) Prior Publication Data
US 2016/0159733 A1 Jun. 9, 2016

(30) Foreign Application Priority Data
Jul. 25, 2013 (JP) .................................. 2013-154948

(51) Int. Cl.
*C07C 69/52* (2006.01)
*C07C 259/04* (2006.01)
(Continued)

(52) U.S. Cl.
CPC ............. *C07C 259/04* (2013.01); *B01J 31/02* (2013.01); *B01J 31/0209* (2013.01);
(Continued)

(58) Field of Classification Search
CPC .................................................... C07C 259/04
(Continued)

(56) References Cited

U.S. PATENT DOCUMENTS

| 2,821,544 A | 1/1958 | Holtschmidt |
| 6,392,001 B1 | 5/2002 | Mertes et al. |
| 2002/0013492 A1 | 1/2002 | Nishioka et al. |

FOREIGN PATENT DOCUMENTS

| CN | 1125719 A | 7/1996 |
| EP | 0 477 376 A1 | 4/1992 |

(Continued)

OTHER PUBLICATIONS

Tadashi Hashimoto et al., Journal of the Society of Rubber Science and Technology, 1972, pp. 452-461, vol. 45, No. 5.

(Continued)

*Primary Examiner* — Deborah D Carr
(74) *Attorney, Agent, or Firm* — Sughrue Mion, PLLC

(57) ABSTRACT

A reaction accelerator is provided which is used in a reaction of a compound including an isocyanate group that is not directly bonded to an aromatic ring in a molecule with a compound including an active hydrogen-containing group and is formed of a compound including a halogenated carbamoyl group. A production method is provided which includes reacting a compound including an isocyanate group that is not directly bonded to an aromatic ring in a molecule with a compound including an active hydrogen-containing group to produce a urethane compound, a thiourethane compound, an amide compound or a urea compound, in which the reaction is performed in the presence of the reaction accelerator.

7 Claims, 6 Drawing Sheets

(51) Int. Cl.
*B01J 31/02* (2006.01)
*C07C 269/02* (2006.01)
*C07C 271/04* (2006.01)
*C07C 271/16* (2006.01)
*C07C 271/20* (2006.01)
*C07C 271/24* (2006.01)
*C07C 231/10* (2006.01)
*C07C 233/18* (2006.01)
*C08F 20/36* (2006.01)
*C07C 263/12* (2006.01)

(52) U.S. Cl.
CPC ....... *B01J 31/0249* (2013.01); *B01J 31/0271* (2013.01); *C07C 231/10* (2013.01); *C07C 233/18* (2013.01); *C07C 263/12* (2013.01); *C07C 269/02* (2013.01); *C07C 271/04* (2013.01); *C07C 271/16* (2013.01); *C07C 271/20* (2013.01); *C07C 271/24* (2013.01); *C08F 20/36* (2013.01); *B01J 2231/643* (2013.01)

(58) Field of Classification Search
USPC .......................................................... 560/223
See application file for complete search history.

(56) References Cited

FOREIGN PATENT DOCUMENTS

| EP | 0 976 723 A2 | 2/2000 |
| EP | 2163540 A1 | 3/2010 |
| GB | 1092134 A | 11/1967 |
| JP | 3-275661 A | 12/1991 |
| JP | 03275661 A * | 12/1991 |
| JP | 5-262715 A | 10/1993 |
| JP | 05262715 A * | 10/1993 |
| JP | 7-304724 A | 11/1995 |
| JP | 9-59244 A | 3/1997 |
| JP | 09059244 A * | 3/1997 |
| JP | 10-45700 A | 2/1998 |
| JP | 11-43527 A | 2/1999 |
| JP | 11043527 A * | 2/1999 |
| JP | 2000-44529 A | 2/2000 |
| JP | 2000044529 A * | 2/2000 |
| JP | 2010-523663 A | 7/2010 |
| KR | 1020070094699 A | 9/2007 |
| WO | 2006049264 A1 | 5/2006 |
| WO | 2008/127584 A1 | 10/2008 |

OTHER PUBLICATIONS

International Search Report for PCT/JP2014/069309 dated Nov. 4, 2014.
Communication dated Nov. 14, 2016, issued by the Korean Intellectual Property Office in corresponding Korean Application No. 10-2016-7001317.
Chinese Office Action issued Nov. 17, 2016, for corresponding Application No. 201480041309.3, 8 pages total (including partial English translation).
R. H. Richter et al: "Isocyanates, Organic" In: "Kirk-Othmer Encyclopedia of Chemical Technology.", Dec. 4, 2000 (Dec. 4, 2000), John Wiley & Sons, Inc., XP055053484, DUI: 10.1002/0471238961.0919150318090308.a01 (28 pgs. total).
Communication dated Feb. 28, 2017, from the European Patent Office in counterpart European Application No. 14828682.6.

* cited by examiner

URETHANIZATION REACTION ACCELERATION OF IPDI (SECONDARY) DUE TO MOC

URETHANIZATION REACTION ACCELERATION OF MDI DUE TO MOC

REACTION ACCELERATOR AND METHOD OF PRODUCING URETHANE COMPOUND, THIOURETHANE COMPOUND, AMIDE COMPOUND, OR UREA COMPOUND USING SAME

CROSS REFERENCE TO RELATED APPLICATIONS

This application is a National Stage of International Application No. PCT/JP2014/069309 filed Jul. 22, 2014 (claiming priority based on Japanese Patent Application No. 2013-154948 filed Jul. 25, 2013), the contents of which are incorporated herein by reference in their entirety.

TECHNICAL FIELD

The present invention relates to a reaction accelerator used for a reaction of a compound including an isocyanate group that is not directly bonded to an aromatic ring with a compound including an active hydrogen-containing group in a molecule, and relates to a method of producing a urethane compound, a thiourethane compound, an amide compound, or a urea compound using the accelerator.

Priority is claimed on Japanese Patent Application No. 2013-154948, filed on Jul. 25, 2013, the content of which is incorporated herein by reference.

BACKGROUND OF THE INVENTION

A reaction of a compound including an isocyanate group that is not directly bonded to an aromatic ring with a compound including an active hydrogen-containing group in a molecule is used to produce a urethane compound, a thiourethane compound, an amide compound, a urea compound or the like.

During the reaction, a catalyst is used to accelerate the reaction. For example, as a catalyst used to react a compound including an isocyanate group that is not directly bonded to an aromatic ring with a compound including a hydroxyl group serving as an active hydrogen-containing group to obtain a urethane compound, an amine-based catalyst or a metal catalyst such as dibutyl tin dilaurate, is normally used (Non Patent document 1).

However, these catalysts have problems in that some substrates do not show reaction accelerating effects sufficiently. When a catalyst remains in a reaction product, this occasionally adversely affects the physical properties of the reaction product or the physical properties of a cured product thereof.

Therefore, in addition to using these catalysts, a technique of accelerating the reaction has been required.

BACKGROUND ART DOCUMENTS

Non Patent Documents

Non Patent document 1: Journal of the Society of Rubber Science and Technology, Japan, 1972, Vol. 45, No. 5, p. 452 to 461

DISCLOSURE OF INVENTION

Problem to be Solved by the Invention

The present invention has been made in consideration of the above-described problem and an object thereof is to provide a reaction accelerator which is capable of accelerating a reaction of a compound including an isocyanate group that is not directly bonded to an aromatic ring with a compound including an active hydrogen-containing group in a molecule thereof, and a method of producing a urethane compound, a thiourethane compound, an amide compound, or a urea compound using the same.

Means for Solving the Problem

As a result of intensive research conducted to solve the above-described problem, the present inventors found that a compound including a halogenated carbamoyl group has an effect of improving reactivity between an isocyanate group of a compound including an isocyanate group in a molecule that is not directly bonded to an aromatic ring with an active hydrogen-containing group.

For example, if a compound including a halogenated carbamoyl group exists in a reaction system when a compound including an isocyanate group that is not directly bonded to an aromatic ring is reacted (urethanization reaction or the like) with a compound including an active hydrogen-containing group, the reaction rate of the reaction (urethanization reaction or the like) increases.

The present invention is based on the above-described knowledge and has the following aspects.

[1] A reaction accelerator, wherein the reaction accelerator is used in a reaction of a compound including an isocyanate group in a molecule, in which the isocyanate group is not directly bonded to an aromatic ring, with a compound including an active hydrogen-containing group, and the reaction accelerator is a compound including a halogenated carbamoyl group.

[2] The reaction accelerator according to [1], in which the reaction is a reaction that generates a urethane compound, a thiourethane compound, an amide compound or a urea compound.

[3] The reaction accelerator according to [1] or [2], in which the compound including an isocyanate group that is not directly bonded to an aromatic ring in a molecule is at least one selected from a group consisting of hexamethylene diisocyanate, trimethyl hexamethylene diisocyanate, lysine diisocyanate, norbornane diisocyanate, trans-cyclohexane-1,4-diisocyanate, isophorone diisocyanate, bis(isocyanate methyl) cyclohexane, dicyclohexylmethane diisocyanate, dimer acid diisocyanate, m-xylene diisocyanate, m-tetramethylxylene diisocyanate, other diisocyanate compounds represented by the general formula OCN—R—NCO (R represents a divalent aliphatic residue having 1 to 20 carbon atoms), methacroyl isocyanate, 3-isopropenyl-α,α-dimethylbenzyl isocyanate, 3-isocyanatepropyl trimethoxysilane, methacryloyloxyethyl isocyanate, acryloyloxyethyl isocyanate, 1,1-(bisacryloyloxymethyl)ethyl isocyanate, methacryloyloxyethoxyethyl isocyanate, acryloyloxyethoxyethyl isocyanate, and other monoisocyanate compounds represented by the general formula R"—NCO (R" represents a monovalent aliphatic residue having 1 to 20 carbon atoms).

[4] The reaction accelerator according to any one of [1] to [3], in which the active hydrogen-containing group is a hydroxyl group, a mercapto group, a carbonyl group, or an amino group.

[5] The reaction accelerator according to any one of [1] to [4], further including a (meth)acryloyl group.

[6] The reaction accelerator according to any one of [1] to [5] which is a compound represented by the following formula (I-1) or (I-2).

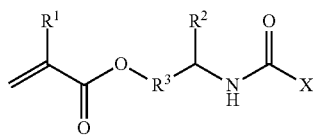

(I-1)

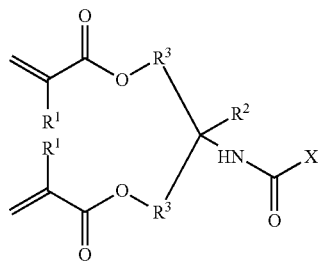

(I-2)

[In the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from a group consisting of an ether bond, an ester bond, and a phenylene bond, X represents a fluorine atom, a chlorine atom, a bromine atom or an iodine atom, and two $R^1$'s in the formula (I-2) may be the same as or different from each other and two $R^3$'s may be the same as or different from each other.]

[7] A production method including: reacting a compound including an isocyanate group that is not directly bonded to an aromatic ring thereof with a compound including an active hydrogen-containing group to produce a urethane compound, a thiourethane compound, an amide compound or a urea compound, in which the reaction is performed in the presence of the reaction accelerator according to any one of [1] to [6].

Effects of the Invention

According to the present invention, it is possible to provide a reaction accelerator which is capable of accelerating a reaction of a compound including an isocyanate group that is not directly bonded to an aromatic ring thereof with a compound including an active hydrogen-containing group in a molecule thereof, and a method of producing a urethane compound, a thiourethane compound, an amide compound or a urea compound using the accelerator.

BEST MODE FOR CARRYING OUT THE INVENTION

Reaction Accelerator

Figure 1:
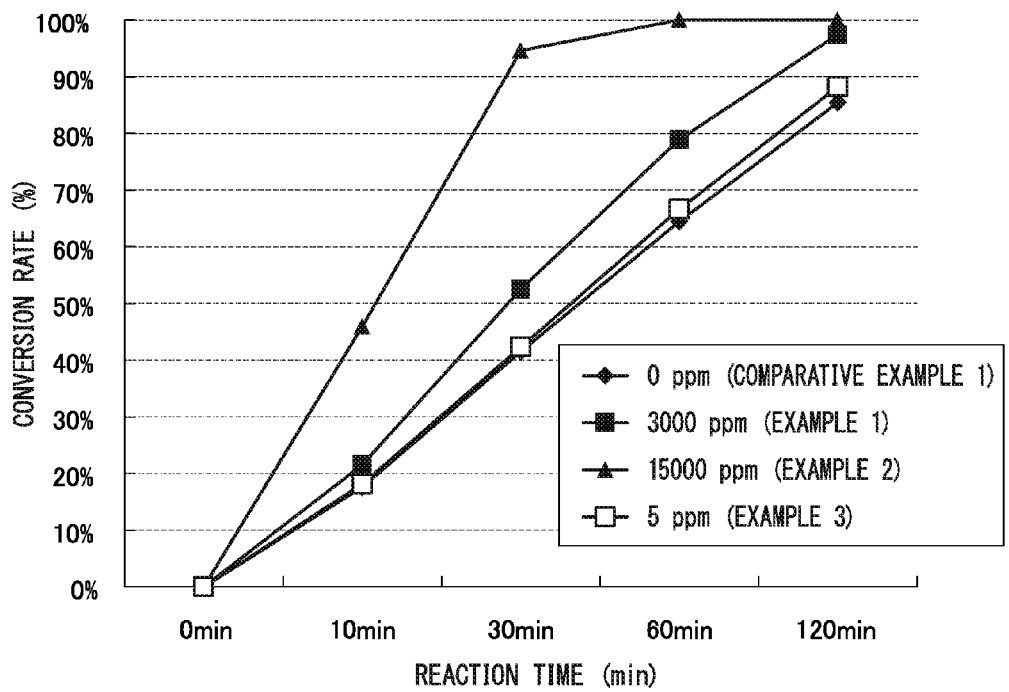
FIG. 1 is a graph showing results of Examples 1 to 3 and Comparative Example 1 in which a urethanization reaction of MOI is performed (change in the conversion ratio of an isocyanate group of MOI to urethane with time (urethanization rate)).

A reaction accelerator of the present invention is a compound including a halogenated carbamoyl group.

In the present invention, the "halogenated carbamoyl group" indicates a group having a structure represented by >N—CO—Z (Z represents a halogen atom). Examples of the halogen atom include a fluorine atom, a chlorine atom, a bromine atom and an iodine atom.

In regard to the reaction accelerator of the present invention, the structure thereof is not particularly limited as long as a halogenated carbamoyl group is included for the function as a reaction accelerator, but it is preferable that the reaction accelerator may further include a (meth)acryloyl group in terms of curing properties. Particularly, it is preferable that the reaction accelerator also include a (meth)acryloyl group when a compound including an isocyanate group that is not directly bonded to an aromatic ring in a molecule includes a (meth)acryloyl group in a molecule at the same time.

A "(meth)acryloyl group" indicates an acryloyl group ($CH_2$=CH—CO—) or a methacryloyl group ($CH_2$=C($CH_3$)—CO—).

As the reaction accelerator including an isocyanate group that is not directly bonded to an aromatic ring and a (meth)acryloyl group in a molecule thereof, a compound represented by the following general formula (I-1) or (I-2) is preferable in terms of the availability of raw materials and reactivity.

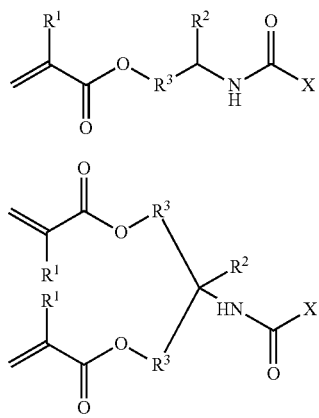

[In the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from a group consisting of an ether bond, an ester bond and a phenylene bond, and X represents a fluorine atom, a chlorine atom, a bromine atom or an iodine atom. Two $R^1$'s in the formula (I-2) may be the same as or different from each other and two $R^3$'s may be the same as or different from each other.]

The alkylene group in the present invention means a group generated by removing two arbitrary hydrogen atoms bonded to a carbon atom in aliphatic saturated hydrocarbon.

As the alkylene group having 1 to 10 carbon atoms, for $R^3$, in the formula (I-1) or (I-2), an alkylene group having 1 to 8 carbon atoms is preferable, an alkylene group having 1 to 6 carbon atoms is more preferable, and an alkylene group having 1 to 4 carbon atoms is still more preferable.

As the alkylene group which can be used for $R^3$, a linear or branched chain alkylene group is preferable and a linear alkylene group is more preferable.

With respect to the alkylene group, a single bond between carbon atoms in the alkylene group may be substituted with a bond selected from a group consisting of an ether bond (—O—), an ester bond (—CO—O—) and a phenylene bond (—$C_6H_4$—). The number of the single bond to be substituted with said bond may be one or two or greater, but is preferably one. In a case where two or more single bonds are substituted, the bonds to be substituted with the respective single bonds may be the same as or different from each other.

Preferable specific examples of the group formed by substituting the alkylene group or a single bond between carbon atoms of the alkylene group with a bond selected from a group consisting of an ether bond, an ester bond, and a phenylene bond include —$CH_2$—, —$C_2H_4$—, —$(CH_2)_3$—, —$(CH_2)_4$—, —$(CH_2)_5$—, —$(CH_2)_6$—, —$CH_2$—O—$C_2H_4$—, —$C_2H_4$—COO—$CH_2$—, and —$C_2H_4$-Ph-$CH_2$—.

With respect to $R^3$, the alkylene group or the group, formed by substituting a single bond between carbon atoms of the alkylene group with a bond selected from a group consisting of an ether bond, an ester bond and a phenylene bond may include a substituent.

Examples of the substituent include a hydrocarbon group, a nitro group, a cyano group, —OR', —COR', and —COOR' (R' represents an alkyl group).

In a case where $R^3$ includes a phenylene bond, the substituent may be provided by substituting a hydrogen atom in an alkylene group or substituting a hydrogen atom in a phenylene bond.

The hydrocarbon group usable as the substituent is not particularly limited and examples thereof include a hydrocarbon group having 1 to 10 carbon atoms. Preferable examples thereof include a hydrocarbon having 1 to 6 carbon atoms and more preferable examples thereof include a methyl group, an ethyl group, a propyl group, an isopropyl group, a butyl group, an isobutyl group, a t-butyl group, a cyclopentyl group, a vinyl group, a cyclohexyl group, and a phenyl group.

As an alkyl group usable as R', an alkyl group having 1 to 10 carbon atoms is an exemplary example. Preferable examples thereof include an alkyl group having 1 to 6 carbon atoms and more preferable examples thereof include a methyl group, an ethyl group, a propyl group, an isopropyl group, a butyl group, an isobutyl group, a t-butyl group and a cyclopentyl group.

As $R^3$, among the aforementioned groups, an alkylene group having 1 to 8 carbon atoms or a group formed by substituting at least one single bond between carbon atoms of the alkylene group with an ether bond is preferable. An alkylene group having 1 to 6 carbon atoms or a group formed by substituting at least one single bond between carbon atoms of the alkylene group with an ether bond is more preferable, and an alkylene group having 1 to 4 carbon atoms or a group formed by substituting at least one single bond between carbon atoms of the alkylene group with an ether bond is still more preferable. Furthermore, —$CH_2$—, —$C_2H_4$—, —$(CH_2)_3$—, —$CH_2$—O—$C_2H_4$—, or —$C_2H_4$—O—$C_2H_4$— is particularly preferable.

X may represent any of a fluorine atom, a chlorine atom, a bromide atom and an iodine atom. Among these, a chlorine atom is preferable.

As a compound represented by the formula (I-1), N-(meth)acryloyloxyethyl carbamoyl chloride, N-(meth)acryloyloxyethoxyethyl carbamoyl chloride or the like is preferable.

As a compound represented by the formula (I-2), N-1,1-(bisacrloyloxymethyl)ethyl carbamoyl chloride or the like is preferable.

The reaction accelerator of the present invention is used for a reaction of a compound including an isocyanate group in a molecule that is not directly bonded to an aromatic ring thereof with a compound including an active hydrogen-containing group.

The reaction rate of these compounds can be improved when the reaction is performed in the presence of the reaction accelerator of the present invention.

<Method of Producing Urethane Compound, Thiourethane Compound, Amide Compound or Urea Compound>

A production method of the present invention is a method of reacting a compound including an isocyanate group (hereinafter, also referred to as an isocyanate compound) that is not directly bonded to an aromatic ring with a compound including an active hydrogen-containing group (hereinafter, also referred to as an active hydrogen-containing compound) to produce a urethane compound, a thiourethane compound, an amide compound or a urea compound, in which the reaction is performed in the presence of the reaction accelerator of the present invention.

[Isocyanate Compound]

A compound including an isocyanate group that is not directly bonded to an aromatic ring is used as an isocyanate compound. The reaction accelerator of the present invention has an excellent effect of accelerating a reaction of such an isocyanate group with an active hydrogen-containing group.

The isocyanate compound is not particularly limited as long as the compound includes an isocyanate group that is not directly bonded to an aromatic ring in a molecule and a compound can be suitably selected from known isocyanate compounds so that a compound having the target structure of is produced by the above-described reaction. The isocyanate compound may or may not have an aromatic ring in a molecule.

As the isocyanate compound, monoisocyanates having one isocyanate group that is not directly bonded to an aromatic ring in a molecule or diisocyanates having two isocyanates that are not directly bonded to an aromatic ring in a molecule are preferable.

Specific examples of the isocyanate compound include diisocyanates such as hexamethylene diisocyanate (HDI), trimethyl hexamethylene diisocyanate (TMXDI), lysine diisocyanate, norbornane diisocyanate (NDI), trans-cyclohexane-1,4-diisocyanate, isophorone diisocyanate (IPDI), bis(isocyanatemethyl)cyclohexane (H6XDI), dicyclohexylmethane diisocyanate (H12MDI), dimer acid diisocyanate (DDI), m-xylene diisocyanate, m-tetramethylxylene diisocyanate, and other diisocyanate compounds represented by the formula OCN—R—NCO (R represents a divalent aliphatic residue having 1 to 20 carbon atoms); and monoisocyanates such as methacryloyl isocyanate (MAI), 3-isopropenyl-α,α-dimethylbenzyl isocyanate (m-TMI), 3-isocyanatepropyl trimethoxysilane, methacryloyloxyethyl isocyanate (MOI), acryloyloxyethyl isocyanate (AOI), 1,1-(bisacryloyloxymethyl)ethyl isocyanate (BEI), methacryloyloxyethoxyethyl isocyanate (MOI-EG), acryloyloxyethoxyethyl isocyanate (AOI-EG), and other monoisocyanate compounds represented by the formula R''—NCO (R'' represents a monovalent aliphatic residue having 1 to 20 carbon atoms).

As R, a linear or branched alkylene group is an exemplary example, and a linear alkylene group is preferable. The number of carbon atoms of R is preferably in a range of 1 to 10 and is more preferably in a range of 4 to 7.

As R'', a linear or branched alkyl group is an exemplary example, and a linear alkyl group is preferable. The number of carbon atoms of R'' is preferably in a range of 1 to 10 and is more preferably in a range of 4 to 7.

A compound including a (meth)acryloyl group is preferable as the isocyanate compound. When an isocyanate compound includes a (meth)acryloyl group, a compound including a (meth)acryloyl group is obtained as a reaction product between the isocyanate compound and an active hydrogen-containing group. Such a compound is polymerizable and a composition containing the compound can be used for a coating material, an ink, an adhesive, and a coating agent as a curable composition.

As the isocyanate compound including an isocyanate group and a (meth)acryloyl group in a molecule, a compound represented by the following general formula (II-1) or (II-2) is preferable in terms of availability of raw materials and reactivity.

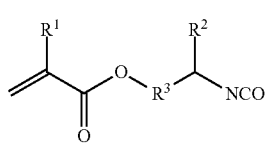

(II-1)

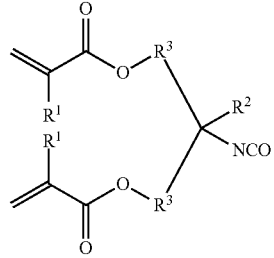

(II-2)

[In the formula, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from a group consisting of an ether bond, an ester bond and a phenylene bond. Two R's in the formula (II-2) may be the same as or different from each other and two $R^3$'s may be the same as or different from each other.]

Structures and preferable scopes of $R^1$, $R^2$, and $R^3$ in the formula (II-1) or (II-2) are the same as the structures and preferable scopes of $R^1$, $R^2$, and $R^3$ in the formula (I-1) or (I-2).

Specific examples of the compound represented by the formula (II-1) include (meth)acryloyloxy methyl isocyanate, (meth)acryloyloxy ethyl isocyanate, (meth)acryloyloxy propyl isocyanate, (meth)acryloyloxy butyl isocyate, (meth)acryloyloxy propyl isocyanate, (meth)acryloyloxy butyl isocyanate, (meth)acryloyloxy pentyl isocyanate, (meth)acryloyloxy hexyl isocyanate, (meth)acryloyloxy heptyl isocyanate, (meth)acryloyloxy octyl isocyanate, (meth)acryloyloxy nonyl isocyanate, (meth)acryloyloxy decyl isocyanate, and (meth)acryloyloxy ethoxy ethyl isocyanate. Among these, in terms of availability of raw materials and reactivity, (meth)acryloyloxy ethyl isocyanate or (meth)acryloyloxy ethoxy ethyl isocyanate is preferable.

Specific preferable examples of the compound represented by the formula (II-2) include 1,1-(bisacryloyloxymethyl)ethyl isocyanate.

[Active Hydrogen-Containing Compound]

The active hydrogen-containing compound includes an active hydrogen-containing group.

The active hydrogen is a hydrogen atom bonded to a nitrogen atom, an oxygen atom, a sulfur atom or the like and has higher reactivity than that of a hydrogen atom bonded to a carbon atom.

The active hydrogen-containing group is not particularly limited as long as the structure thereof has active hydrogen, but a hydroxyl group, a mercapto group, a carboxyl group, or an amino group is preferable and a hydroxyl group is particularly preferable in terms of reactivity.

Examples of the compound having a hydroxyl group as an active hydrogen-containing group include monoalcohols such as $R^4OH$ ($R^4$ represents an alkyl group having 1 to 10 carbon atoms); hydroxyalkyl (meth)acrylate such as 2-hydroxyethyl (meth)acrylate, hydroxypropyl (meth)acrylate, 2,3-dihydroxybutyl (meth)acrylate, 4-hydroxybutyl (meth)acrylate, 6-hydroxyhexyl (meth)acrylate, or 8-hydroxyoctyl (meth)acrylate; vinyl ethers such as 2-hydroxyethyl vinyl ether and 4-hydroxybutyl vinyl ether; a monoesterified product obtained from polyhydric alcohol and (meth)acrylic acid such as 4-hydroxymethyl cyclohexyl (meth)acrylate or polyalkylene glycol mono(meth)acrylate; a hydroxyl group-containing compound obtained by performing ring-opening polymerization of ε-caprolactone, ethylene oxide or propylene oxide with the above-described monoesterified product of a polyhydric alcohol and (meth)acrylic acid; polyhydric alcohol such as ethylene glycol, diethylene glycol, triethylene glycol, propylene glycol, dipropylene glycol, 1,3-butylene glycol, 1,4-butylene glycol, glycerin, diglycerin, D-glucose, D-glucitol, isopropylene glycol, butanediol, 1,5-pentanediol, 1,6-hexanediol, 1,9-nonanediol, or neopentyl glycol; polyalkylene glycols such as polyethylene glycol, polypropylene glycol, polybutylene glycol, and polytetramethylene glycol; and polymer polyols such as polycaprolactonediol, polycaprolactone triol and polycarbonate diol.

Examples of the compound having a mercapto group as an active hydrogen-containing group include monothiol such as 1-butanethiol, 1-pentane thiol, 1-octanethiol, 1-dodecanethiol, n-octanedecanethiol, α-toluenethiol, 2-benzimidazole thiol, 2-thiazoline-2-thiol, 2-methyl-2-propanethiol, or O-aminothiophene; and polyvalent thiol such as hexane dithiol, decane dithiol, 1,4-butanediol bisthiopropionate, 1,4-butanediol bisthioglycolate, ethylene glycol bisthioglycolate, ethylene glycol bisthiopropionate, trimethylol propane tristhioglycolate, trimethylol propane tristhiopropionate, trimethylol propane tris(3-mercaptobutyrate), pentaerythritol tetrakis thioglycolate, pentaerythritol tetrakis thiopropionate, trimercaptopropionic acid tris(2-hydroxyethyl) isocyanurate, 1,4-dimethylmercaptobenzene, 2,4,6-trimercapto-s-triazine, 2-(N,N-dibutylamino)-4,6-dimercapto-s-triazine, tetraethylene glycol bis 3-mercaptopropionate, trimethylol propane tris 3-mercaptopropionate, tris(3-mercaptopropinyloxyethyl) isocyanurate, pentaerythritol tetrakis 3-mercaptopropionate, dipentaerythritol tetrakis 3-mercaptopropionate, 1,4-bis(3-mercaptobutyloxy) butane, 1,3,5-tris(3-mercaptobuytloxyethyl)-1,3,5-triazine-2,4,6(1H,3H,5H)-trione, or pentaerythritol tetrakis (3-mercaptobutyrate).

Examples of the compound having a carboxyl group as an active hydrogen-containing group include monocarboxylic acid such as acetic acid or propionic acid; aliphatic or aromatic polycarboxylic acid such as succinic acid, adipic acid, dimer acid, phthalic acid, isophthalic acid, terephthalic acid, trimellitic acid, or pyromellitic acid; and polymer polycarboxylic acid such as a (co)polymer of polyamic acid and acrylic acid.

Examples of the compound having an amino group as an active hydrogen-containing group include monoamine such as butylamine, hexylamine, or aniline; aliphatic polyamine such as diethylene triamine, triethylene tetramine, 1,3- or 1,4-bisaminomethylcyclohexane, isophorone diamine, hexamethylene diamine, or bis(4-aminocyclohexyl) methane; aromatic polyamine such as m- or p-xylylene diamine, bis(4-aminophenyl) methane, or 2,4- or 2,6-trylene diamine; glycosamines such as chitosane; and a silicone compound such as bis(3-aminopropyl)polydimethyl siloxane, or bis(3-aminopropyl)polydiphenyl siloxane.

[Reaction of Isocyanate Compound with Active Hydrogen-Containing Compound]

A reaction of an isocyanate compound with the active hydrogen-containing compound can be performed according to a method of adding the active hydrogen-containing compound to a composition that contains an isocyanate compound and a reaction accelerator at a predetermined reaction temperature, a method of adding an isocyanate compound to the composition that contains the active hydrogen-containing compound and the reaction accelerator at a predetermined reaction temperature, or the like.

The reaction temperature during the reaction of an isocyanate compound with an active hydrogen-containing compound is preferably in a range of 40° C. to 80° C. and more preferably in the range of 50° C. to 70° C. In a case where an isocyanate compound has a double bond (for example, in a case where an isocyanate compound includes a (meth)acryloyl group) and the reaction temperature is 80° C. or higher, there is a possibility that the reactivity of the double bond is increased so that a polymerization reaction is promoted, which is not preferable. Meanwhile, when the reaction temperature is 40° C. or lower, the reaction speed is reduced, which is not preferable.

The reaction time is not particularly limited and can be suitably set according to the state in which the reaction is promoted.

As a method of producing the composition containing an isocyanate compound and a reaction accelerator, a method (i) of adding a reaction accelerator to an isocyanate compound or a method (ii) of generating a reaction accelerator as a by-product when an isocyanate compound is produced such that the reaction accelerator coexists in a reaction product is an exemplary example. According to such methods, it is possible to produce a mixture of an isocyanate compound and a reaction accelerator.

As a method of producing a composition containing an active hydrogen-containing compound and a reaction accelerator, a method (iii) of adding a reaction accelerator to an active hydrogen-containing compound is an exemplary example.

In the method (i) or (iii), commercially available products may be respectively used for the isocyanate compound, the active hydrogen-containing compound and the reaction accelerator, and products which are produced by a known production method may be used.

Examples of the commercially available products of the isocyanate compound include Karenz MOI (registered trademark, manufactured by Showa Denko K.K., methacryloyloxy ethyl isocyanate), Karenz AOI (registered trademark, manufactured by Showa Denko K.K., acryloyloxy ethyl isocyanate), Karenz MOI-EG (registered trademark, manufactured by Showa Denko K.K., methacryloyloxy ethoxy ethyl isocyanate), and Karenz BEI (registered trademark, manufactured by Showa Denko K.K., 1,1-(bisacryloyloxymethyl)ethyl isocyanate).

A method described in U.S. Pat. No. 2,821,544A is an exemplary example as the method of producing the isocyanate compound.

Examples of the method of producing a reaction accelerator include a method of blowing hydrogen chloride gas to a compound having a (meth)acryloyl group and an isocyanate group and extracting a deposited solid (reaction accelerator) to produce the reaction accelerator; and a method of generating the reaction accelerator as a by-product using phosgene or hydrogen chloride during a process of synthesizing an isocyanate compound to obtain a reaction accelerator as a mixture of the reaction accelerator with the isocyanate compound.

In a case of the method (ii), the reaction accelerator can be generated by adding a halogenated compound to a reaction system during the process of producing an isocyanate compound and changing the isocyanate group in the isocyanate compound into a halogenated carbamoyl group. Further, in the case of this method, a structure other than the isocyanate group of the isocyanate compound is the same as a structure other than the halogenated carbamoyl group of the reaction accelerator.

In the method (ii), a known production method described above can be employed as the method of producing an isocyanate compound.

Examples of the halogen compound to be used to change the isocyanate group to the halogenated carbamoyl group include phosgene and hydrogen chloride.

In the method (i) or (ii), as a method of producing a mixture of an isocyanate compound and a reaction accelerator after the process of producing the reaction accelerator, the following methods 1) and 2) are exemplary examples.

1) A method of blowing hydrogen chloride gas to a compound having a (meth)acryloyl group and an isocyanate group, extracting a deposited solid (reaction accelerator) to produce a reaction accelerator, and then mixing the reaction accelerator with the isocyanate compound.

2) A method of generating a reaction accelerator as a by-product using phosgene or hydrogen chloride during a process of synthesizing an isocyanate compound to obtain a mixture of the isocyanate compound and the reaction accelerator.

The amount of the reaction accelerator during the reaction of an isocyanate compound with an active hydrogen-containing compound is preferably in a range of 5 ppm by mass to 20000 ppm by mass, more preferably in a range of 5 ppm by mass to 8000 ppm by mass, and is still more preferably in a range of 5 ppm by mass to 3000 ppm by mass as a ratio of the amount of the reaction accelerator with respect to the amount (100% by mass) of the isocyanate compound in the reaction system.

In a case where the ratio of the amount of the reaction accelerator to the amount of the isocyanate compound is less than 5 ppm by mass, the reaction acceleration effects may not be sufficiently obtained.

In a case where the ratio of the amount of the reaction accelerator to the amount of the isocyanate compound exceeds 20000 ppm by mass, reactions of an isocyanate group and a (meth)acryloyl group when the isocyanate compound further includes a (meth)acryloyl group are both accelerated and inconvenience may be experienced. As a method of using a compound having two different kinds of reactive functional groups of an isocyanate group and a (meth)acryloyl group, a method of performing a reaction at two stages, that is, performing a reaction (urethanization reaction or the like) of an isocyanate group and an active hydrogen-containing group of an active hydrogen-containing compound and then performing a reaction of a (meth)acryloyl group (radical polymerization reaction or the like) is frequently used. However, when a large amount of a reaction accelerator is present, the second stage of reaction may occur during the first stage of reaction or during storage before the first stage of reaction, thereby an unwanted reaction product may be generated. Accordingly, depending on the method of using an isocyanate compound, it is preferable that the amount of the reaction accelerator to be added is set to 20000 ppm by mass or less and particularly 8000 ppm by mass or less with respect to the amount of the isocyanate compound.

The reaction accelerator for the reaction may be used alone or in combination of two or more kinds thereof.

The following two kinds of measurement methods 1 and 2 are exemplary examples as a method of acquiring the ratio of the amount of the reaction accelerator to the amount (100% by mass) of the isocyanate compound in the reaction system. Further, the following measurement conditions (the amount of samples to be used, the kind of reagent, an NMR machine, the number of times of integration of NMR, and the like) are merely examples and the conditions may be appropriately changed if necessary (particularly in a case where the amount of the reaction accelerator to be contained is small, the conditions of the measurement method 2 may need to be changed into those with high precision).

Measurement Method 1: Silver Nitrate Titration Method (Reference: JIS K1603-3)

A 100 mL methanol aqueous solution (water:methanol=3:7) and 10 g of a sample to be measured are added to a 200 mL capacity beaker and the mixture is stirred and dissolved. The solution is titrated by a silver nitrate aqueous solution (0.02 mol/L, titer 1.006, manufactured by Kanto Kagaku), the equivalent point is measured, and the amount of the reaction accelerator in the sample is acquired using the following formula.

Amount (%) of reaction accelerator$(B)$=(titration value$(L)$ of silver nitrate aqueous solution×titer 1.006×molecular weight of chloride 35.46 (g/mol)×molar concentration of silver nitrate aqueous solution 0.02(mol/L)×100)/amount of samples(g)

[Measurement Method 2: NMR Measurement]

(Conditions)

100 mg of a sample to be measured is dissolved in 0.3 mL of dehydrated benzene d6 in a 5 mmΦ NMR sample tube to prepare a sample for measurement and a $^1$H-NMR spectrum of the sample for measurement is measured under the following conditions.

Device: Avance-400, manufactured by Bruker BioSpin Corporation

Measurement temperature: room temperature

Pulse width: 30°

Pulse repetition time: 5 seconds

Number of times of integration: 128 times (Quantitative Method)

Hereinafter, a method of acquiring the amount of the reaction accelerator from NMR using samples to be measured in which the isocyanate compound is methacryloyloxy ethyl isocyanate (hereinafter, referred to as MOI) and the reaction accelerator is methacryloyloxy ethyl carbamoyl chloride (hereinafter, referred to as MOC) is shown below as an example.

Figure 9:
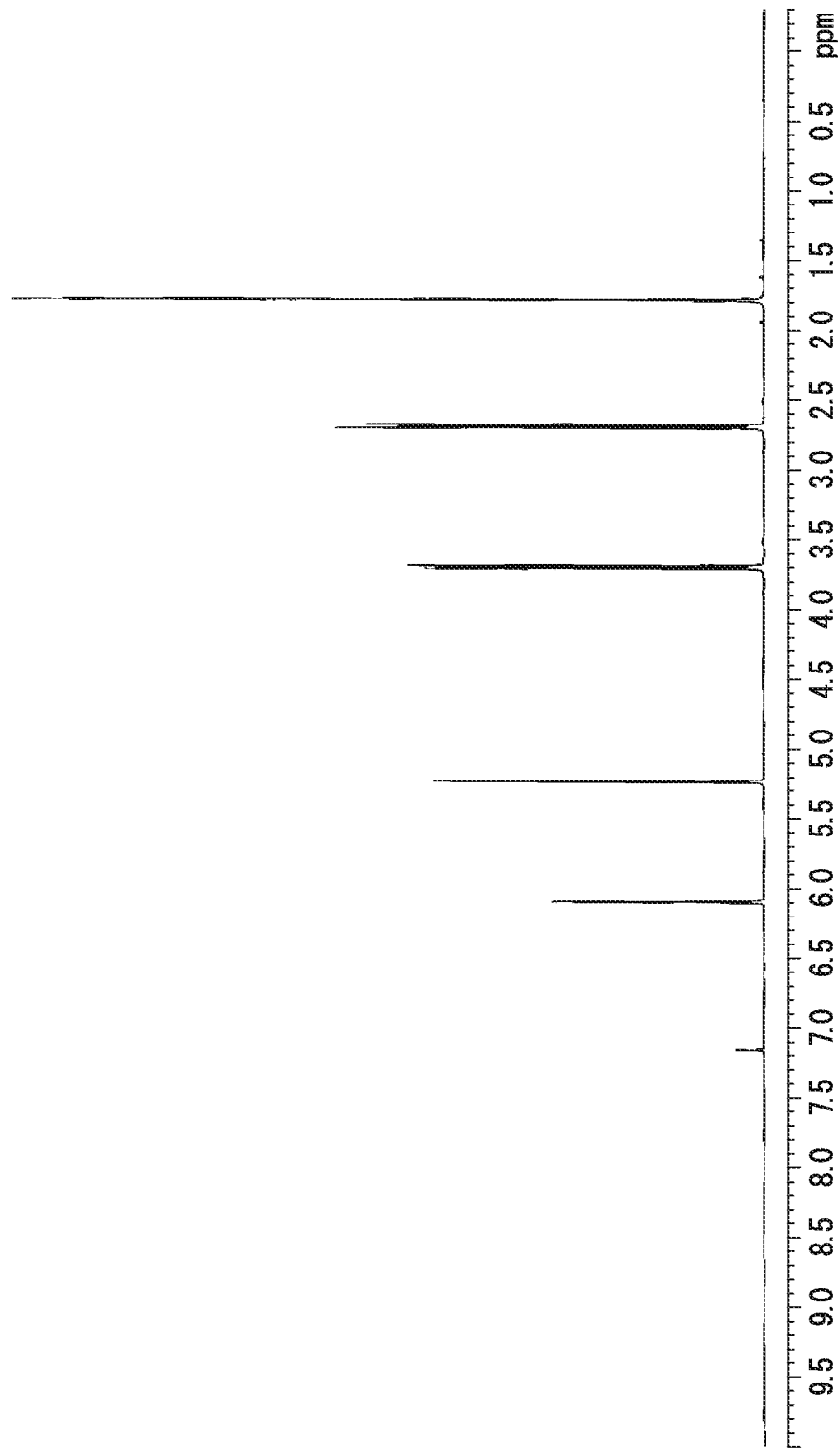
FIG. 9 is an NMR chart of a composition including MOI as an isocyanate compound and MOC as a reaction accelerator.
Figure 10:
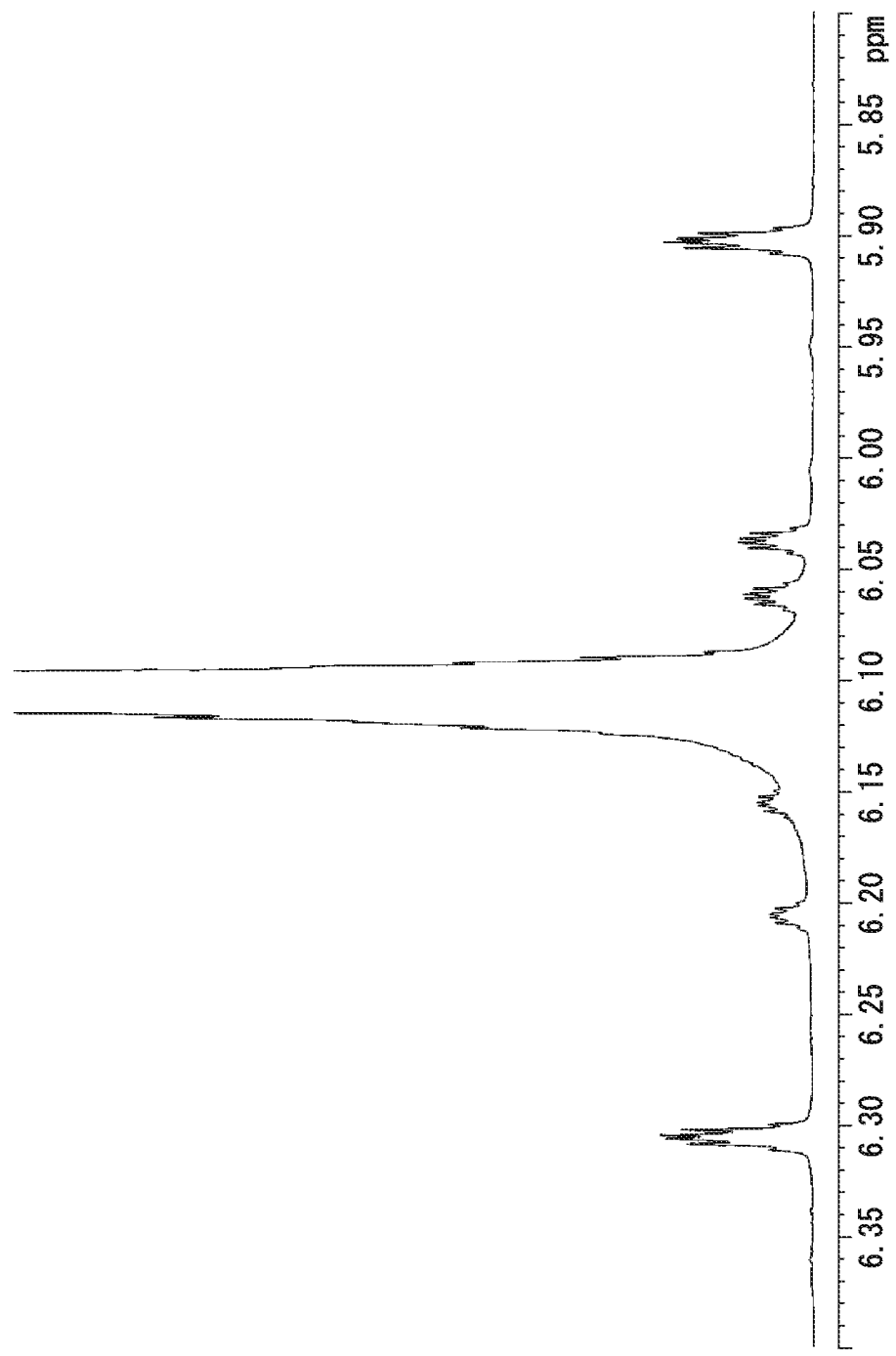
FIG. 10 is a partially enlarged view showing a range of around 5.85 to 6.35 of δ (ppm) of the NMR chart shown in FIG. 9.

NMR charts of the mixture are shown in FIGS. 9 and 10 (wherein the charts are spectra of a composition containing MOI and MOC and the content ratio of MOC to MOI is 3330 ppm by mass). FIG. 9 is an NMR chart (horizontal axis: δ (chemical shift) and vertical axis: signal intensity) showing a range of around 0.5-9.5 of δ (ppm) obtained by performing NMR measurement using tetramethylsilane (TMS) as an internal reference substance. FIG. 10 is an enlarged view showing a range of around 5.85 to 6.35 of δ (ppm) of the NMR chart shown in FIG. 9.

In the present chart, a peak detected in a range of around of 2.2 to 4.3 of δ (ppm) is a peak corresponding to four protons of an ethylene group included in both of MOI and MOC. Meanwhile, the integration value of a peak in a range of 6.02 to 6.05 of δ (ppm) corresponds to two protons on the terminal of a methacrylic group of MOC.

Samples are prepared by adding various amounts of the reaction accelerator in a range of 100 ppm by mass to 3330 ppm by mass in the isocyanate compound and uniformly dissolving 100 mg of the samples in 0.3 mL of dehydrated benzene d6, and respective $^1$H-NMR spectra are measured under the above-described conditions. A calibration curve of an intensity ratio regarding the two peaks described above with respect to the amount of MOC to be added is created based on the aforementioned measured values.

The amount of MOC contained in a composition is acquired by measuring NMR of the composition to be measured under the same conditions as those described above and plotting the above-described calibration curve.

In regard to the amount of the isocyanate compound and the active hydrogen-containing compound in the reaction, the molar ratio of the isocyanate group included in an isocyanate compound to the active hydrogen-containing group included in an active hydrogen-containing compound (isocyanate group:active hydrogen-containing group) is preferably in a range of 1:3 to 3:1 and is more preferably in a range of 1.2:1 to 1:1.2.

Each of the isocyanate compound and the active hydrogen-containing compound used in the reaction may be used alone or in combination of two or more kinds thereof.

[Combination of Isocyanate Compound and Reaction Accelerator]

In the present invention, it is preferable that a structure in which an isocyanate group is removed from at least one kind of isocyanate compound used in the reaction is the same as a structure in which a halogenated carbamoyl group is removed from at least one kind of reaction accelerator.

For example, in a case where the isocyanate compound includes a compound represented by the formula (II-1), it is preferable that the reaction accelerator contains a compound which is represented by the formula (I-1) and in which $R^1$, $R^2$, and $R^3$ in the formula (I-1) are respectively the same as $R^1$, $R^2$, and $R^3$ included in the isocyanate compound. In a case where the isocyanate compound contains a compound represented by the formula (II-2), it is preferable that the reaction accelerator contains a compound which is represented by the formula (I-2) and in which $R^1$, $R^2$, and $R^3$ in the formula (I-2) are respectively the same as $R^1$, $R^2$, and $R^3$ included in the isocyanate compound.

As described above, when the structure in which an isocyanate group is removed from the isocyanate compound is the same as the structure in which a halogenated carbamoyl group is removed from the reaction accelerator, the yield of a target reaction product is improved in a reaction of, for example, the isocyanate compound with an active hydrogen-containing group described below.

[Optional Components]

Other components (optional components) other than the isocyanate compound, the active hydrogen-containing compound, and the reaction accelerator may be added to the reaction system during the reaction of the isocyanate compound and the active hydrogen-containing compound.

A polymerization inhibitor is an exemplary example as an optional component. As the polymerization initiator, a phenolic compound generally used to prevent polymerization or a hydroquinone-based compound can be used and specific examples thereof include hydroquinone, methoxyhydroquinone, catechol, p-tert-butylcatechol, cresol, dibutyl hydroxy toluene (BHT), and 2,4,6-tri-tert-butylphenol.

For the purpose of dilution, an inactive solvent may be contained as an optional component because it is easily handled. An inactive solvent is a solvent which does not contain active hydrogen and examples thereof include toluene, xylene, hexane, ethyl acetate, tetrahydrofuran, n-butyl acetate, cyclohexanone and methyl isobutyl ketone.

In addition, a curing catalyst (a thermal curing catalyst or a photo-curing catalyst), a photo-radical initiator, a curing agent, a curing accelerator, or an additive (a filler, a defoaming agent, a flame retardant, an antioxidant, an ultraviolet absorber, a stress reducing agent, a flexibility imparting agent, waxes, a resin, a crosslinking agent, a halogen trapping agent, a leveling agent, or a wetting properties-improving agent) may be included as needed.

Examples of the curing catalyst include a thermal acid generator and a photoacid generator. As the thermal acid generator or the photoacid generator, diazonium salts, iodonium salts, sulfonium salts, phosphonium salts, selenium salts, oxonium salts, or ammonium salts can be used. The curing catalyst may be used alone or in combination of two or more kinds thereof.

The amount of the curing catalyst to be added is in a range of 0.05 parts by mass to 10 parts by mass and preferably in a range of 0.5 parts by mass to 5 parts by mass with respect to 100 parts by mass of the total amount of the composition.

Examples of the photo-radical initiator include benzophenone, benzyl acetophenone, benzyl dimethyl ketone, benzoin, benzoin methyl ether, benzoin ethyl ether, benzoin isopropyl ether, dimethoxy acetophenone, dimethoxy phenyl acetophenone, diethoxy acetophenone, diphenyl disulfite, methyl ortho-benzoyl benzoate, ethyl 4-dimethylaminobenzoate, 2,4-diethyl thioxanthone, 2-methyl-1-(4-methylthiophenyl)-2-morpholinopropan-1-one, 3,3',4,4'-tetra(t-butylperoxycarbonyl)benzophenone, 2-hydroxy-2-methyl-1-phenyl-propane-1-one, 4,4-bisdiethylaminobenzophenone, and 2,2'-bis(2-chlorophenyl)-4,5,4',5'-tetraphenyl-1,2'-biimidazole. One kind may be used alone or a combination of two or more kinds thereof may be used and a photosensitizer may be added if necessary.

Examples of the curing agent include a phenolic resin and an acid anhydride.

As a phenolic resin, a resin in which phenol or cresol is polymerized using formaldehyde can be used. The resin may be a resin obtained by copolymerizing an alicyclic compound or an aromatic compound such as dicyclopentadiene, naphthalene, or biphenyl. The amount of the phenolic resin to be mixed is normally in a range of 0 part by mass to 200 parts by mass and can be suitably selected within a range of 5 parts by mass to 200 parts by mass with respect to 100 parts by mass of the total amount of the composition.

A polybasic acid anhydride is an exemplary example of an acid anhydride, and specific examples thereof include phthalic anhydride, trimellitic anhydride, pyromellitic anhydride, a benzophenone tetracarboxylic anhydride, 4-tetrahydrophthalic anhydride, 4-methyl-4-tetrahydrophthalic anhydride, 3-methyl-4-tetrahydrophthalic anhydride, nadic anhydride, methyl nadic anhydride, a hydrogenated methyl nadic anhydride, 4-(4-methyl-3-pentenyl)tetrahydrophthalic anhydride, succinic anhydride, adipic anhydride, maleic anhydride, sebacic anhydride, dodecanedioic anhydride, a methyl cyclohexene tetracarboxylic anhydride, dodecenyl succinic anhydride, hexahydrophthalic anhydride, 4-methylhexahydrophthalic anhydride, 3-methylhexahydrophthalic anhydride, a vinyl ether-maleic anhydride copolymer, and an alkyl styrene maleic anhydride copolymer. The amount of the acid anhydride to be mixed is normally in a range of 0 parts by mass to 160 parts by mass and can be suitably selected within a range of 20 parts by mass to 160 parts by mass with respect to 100 parts by mass of the total amount of the composition.

The curing accelerator is not particularly limited as long as the agent is normally used, and examples thereof include a diazabicycloundecene-based curing accelerator (diazabicycloalkenes); a phosphorus-based curing accelerator such as phosphoric acid ester or phosphines; and an amine-based curing accelerator such as a tertiary amine or quaternary ammonium salts. Examples of the diazabicycloundecene-based accelerator include 1,8-diazabicyclo[5,4,0]undecene-7 (DBU) and salts thereof (organic acid salts such as octylate, sulfonate, ortho-phthalate, or phenate).

Specific examples of other curing accelerators include known compounds, for example, a tertiary amine such as benzyldimethylamine, 2,4,6-tris(dimethylaminomethyl) phenol, trimethylamine, or triethylene diamine; imidazoles such as 2-ethyl-4-methyl imidazole, and 1-cyanoethyl-2-ethyl-4-methylimidazole; a phosphorus compound (phosphonium salts or the like) which does not contain an aromatic group such as tetra-n-butylphosphonium-O,O-diethylphosphorodithioate; tertiary amine salts; quaternary ammonium salts; an organic tin compound such as tin octylate, dibutyl tin diacetate, dibutyl tin dilaurate, dibutyl tin oxide, or dioctyl tin oxide; and metal salts, for example, an organic bismuth compound such as bismuth octylate or bismuth decanoate. Moreover, metal organic acid salts can be used together with organic acid salts of the above-described diazabicycloalkenes. Examples of the metal organic acid salts include tin octylate, tin naphthenate, zinc octylate, and zinc naphthenate.

The amount of the curing accelerator can be suitably selected within a range of 0.00001 parts by mass to 5 parts by mass with respect to 100 parts by mass of the total amount of the composition.

Fine particles such as glass fine particles, metal oxide fine particles, rubber fine particles, or ceramic fine particles may be mixed in the reaction system. In addition, fibers such as glass fibers or Kepler fibers may be mixed. One kind may be used alone or a combination of two or more kinds thereof may be used.

The reaction product generated by the reaction of the isocyanate compound with the active hydrogen-containing compound has a structure in which the isocyanate compound is connected to the active hydrogen-containing compound through a bond formed by the reaction of an isocyanate group with an active hydrogen-containing group.

In the reaction of an isocyanate group with an active hydrogen-containing group, a urethane bond (—NH—CO—O—) is formed when the active hydrogen-containing group is a hydroxyl group, a thiourethane bond (—NH—CO—S—) is formed when the active hydrogen-containing group is a mercapto group, an amide bond (—NH—CO—) is formed when the active hydrogen-containing group is a carboxyl group, and a urea bond (—NH—CO—NH—) is formed when the active hydrogen-containing group is an amino group.

Therefore, in a case where the active hydrogen-containing compound includes a hydroxyl group, a mercapto group, a carboxyl group, or an amino group as an active hydrogen-containing group, the above-described reaction is a reaction of generating a urethane compound, a thiourethane compound, an amide compound, or a urea compound (a urethanization reaction, a thiourethanization reaction, an amidation reaction, or a urea reaction).

In the case where the isocyanate compound further includes a (meth)acryloyl group, the reaction product of the reaction includes a (meth)acryloyl group derived from the isocyanate compound.

The reaction product can be used as a curable component constituting a curable composition. When a treatment of irradiating the curable composition containing the reaction product (further containing a radical polymerization initiator, other polymerizable compounds, and the like if necessary) with light or ultraviolet (UV) rays is further performed, radical polymerization of a polymerizable compound such as the reaction product is promoted in the curable composition, thereby obtaining a cured product.

Such a curable composition can be used as coating materials, inks, adhesives, coating agents, electronic materials (liquid resists, film resists, color filter resists, tapes for a semiconductor, gluing agents, and adhesives), printing (press plates and color calibration), medical care items (soft contact lenses and dental materials), fibers, paper, and wood (surface treatment agents), automobiles (top coats, coating materials for repair, and coating materials for a component), consumer electrical appliances (substrates and insulating materials), and building materials (cement primer, coating materials, and adhesives).

EXAMPLES

Hereinafter, the present invention will be described in detail with reference to examples, but the present invention is not limited to these examples.

In respective examples described below, "%" indicates "% by mass" (wt %) and "ppm" indicates "ppm by mass" (wt ppm) unless otherwise noted.

The conditions of liquid chromatography analysis (hereinafter, referred to as "LC analysis") are as follows.

Column: trade name: "Shodex (registered trademark) KF-801" manufactured by Showa Denko K.K., four columns Eluent: tetrahydrofuran (THF)
Flow rate: 0.8 mL/min
Oven temperature: 40° C.
Detector: differential refractive index (RI), UV (wavelength of 210 nm)
(Method of Preparing Reaction Accelerator)

Synthesis Example 1

10.0 g of methacryloyloxy ethyl isocyanate (Karenz MOI (registered trademark), Showa Denko K.K., hereinafter, referred to as "MOI") was added to a 100 mL three-neck flask and 2.58 g of dry hydrogen chloride was bubbled to the methacryloyloxy ethyl isocyanate through an inner intubation while the inner temperature of the flask was decreased to 15° C., thereby obtaining 12.6 g of methacryloyloxy ethyl carbamoyl chloride (hereinafter, referred to as "MOC"). The purity was 100%.

Synthesis Example 2

110 g of aminoethyl methacrylate hydrochloride (hereinafter, referred to as "AEMHCl") was added to 200 g of toluene, 110 g of phosgene was supplied thereto in a state in which AEMHCl was melted at an inner temper of 85° C., and MOI was synthesized. The dissolved phosgene was removed by bubbling nitrogen to a reaction solution and toluene serving as a solvent was distilled under reduced pressure, thereby obtaining 110 g of crude MOI.

When the amount of MOC in the crude MOI was confirmed using silver nitrate titration, the value was 10.8%.
(Effects of Accelerating Urethanization Reaction Due to Addition of Reaction Accelerator)

Example 1

6.21 g of MOI, 0.0186 g (corresponding to 3000 ppm with respect to MOI) of methacryloyloxy ethyl carbamoyl chloride (hereinafter, referred to as "MOC") produced in Synthesis Example 1, 50 mL of toluene, and 0.1 g of BHT were added to a 100 mL three-neck flask and the mixture was stirred and mixed. The obtained mixture was heated to 60° C., 8.89 g of n-butanol was further added to the system, and a reaction of MOI with n-butanol (urethanization reaction) was carried out. During the reaction, the temperature of the reaction solution was held at 60° C.

The time point when n-butanol was added was set as 0 time in the reaction described above, the reaction solution was sampled at respective time points when elapsed times (reaction times) from 0 time were 0 minute, 10 minutes, 30 minutes, 60 minutes, and 120 minutes, LC analysis was performed, and the rate (conversion rate) of MOI, in which an isocyanate group was converted into urethane, from used MOI was acquired based on the following formula. The amount (%) of MOI in the reaction solution was measured by LC analysis. The results are listed in Table 1 and shown in FIG. 1.

Conversion rate (%)=(amount (%) of MOI in prepared solution [before reaction]−amount (%) of MOI in reaction solution at sampling time)/(amount (%) of MOI in prepared solution [before reaction])×100

Example 2

The urethanization reaction was performed and the conversion rate was measured in the same manner as in Example 1 except that the amount of MOC to be added was changed to 0.0932 g (corresponding to 15000 ppm with respect to MOI). The results are listed in Table 1 and shown in FIG. 1.

Example 3

The urethanization reaction was performed and the conversion rate was measured in the same manner as in Example 1 except that the amount of MOC to be added was changed to 0.03 g (corresponding to 5 wt ppm with respect to MOI). The results are listed in Table 1 and shown in FIG. 1.

Comparative Example 1

The urethanization reaction was performed and the conversion rate was measured in the same manner as in Example 1 except that MOC was not added. The results are listed in Table 1 and shown in FIG. 1.

Example 4

Figure 2:
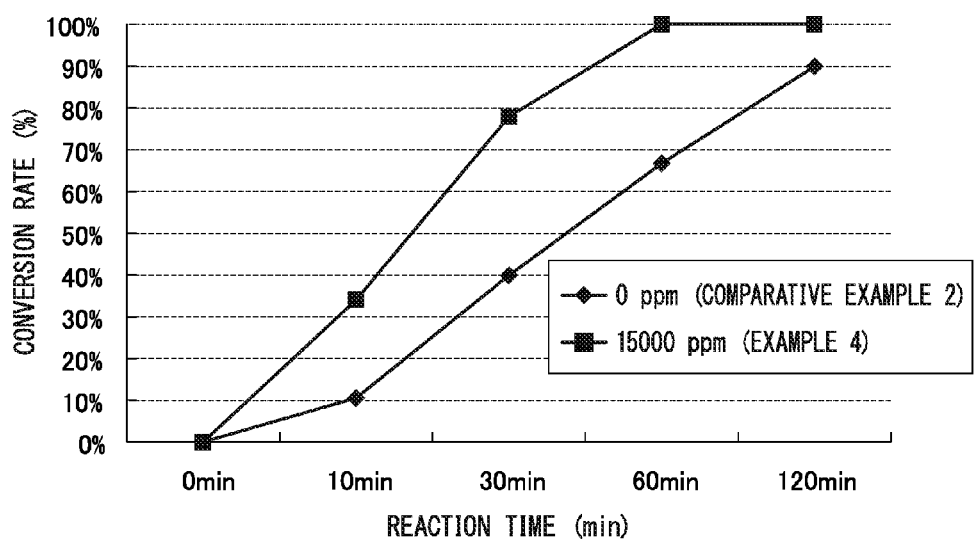
FIG. 2 is a graph showing results of Example 4 and Comparative Example 2 in which a urethanization reaction of AOI is performed (change in the conversion ratio of an isocyanate group of AOI to urethane with time (urethanization rate)).

The urethanization reaction was performed and the conversion rate (rate of AOI, in which an isocyanate group was converted into urethane, from used AOI) was measured in the same manner as in Example 1 except that MOC was changed to 5.64 g of acryloyloxy ethyl isocyanate (Karenz AOI (registered trademark), manufactured by Showa Denko K.K., hereinafter, referred to as "AOI") and the amount of MOC to be added was changed to 0.0846 g (corresponding to 15000 ppm with respect to AOI). The results are listed in Table 1 and shown in FIG. 2.

Comparative Example 2

The urethanization reaction was performed and the conversion rate was measured in the same manner as in Example 4 except that MOC was not added. The results are listed in Table 1 and shown in FIG. 2.

TABLE 1

| | Isocyanate compound | MOC content (ppm) | Conversion rate | | | | |
|---|---|---|---|---|---|---|---|
| | | | 0 min | 10 min | 30 min | 60 min | 120 min |
| Comparative Example 1 | MOI | 0 | 0.0% | 17.6% | 41.5% | 64.4% | 85.4% |
| Example 1 | | 3000 | 0.0% | 21.5% | 52.5% | 78.9% | 97.4% |
| Example 2 | | 15000 | 0.0% | 45.9% | 94.6% | 100.0% | 100.0% |
| Example 3 | | 5 | 0.0% | 18.1% | 42.3% | 66.6% | 88.2% |
| Comparative Example 2 | AOI | 0 | 0.0% | 10.5% | 39.9% | 66.7% | 89.9% |
| Example 4 | | 15000 | 0.0% | 34.0% | 77.9% | 100.0% | 100.0% |

From the above-described results, it was confirmed that MOC functioned as a reaction accelerator in the reaction of isocyanate with alcohol (urethanization reaction).

(Effects of Accelerating Amidation Reaction Due to Addition of Reaction Accelerator)

Example 5

0.0932 g (corresponding to 15000 ppm with respect to MOI described below) of MOC produced in Synthesis Example 1, 6.89 g of decanoic acid, 64.52 g of propylene glycol monomethyl ether acetate (PGMAc), and 0.1 g of BHT were added to a 100 mL three-neck flask and the mixture was stirred and mixed. The obtained mixture was heated to 60° C., 6.21 g of MOI (Karenz MOI (registered trademark), manufactured by Showa Denko K.K.) was further added to the system, and a reaction of MOI with decanoic acid (amidation reaction) was carried out. During the reaction, the temperature of the reaction solution was maintained at 60° C.

Figure 3:
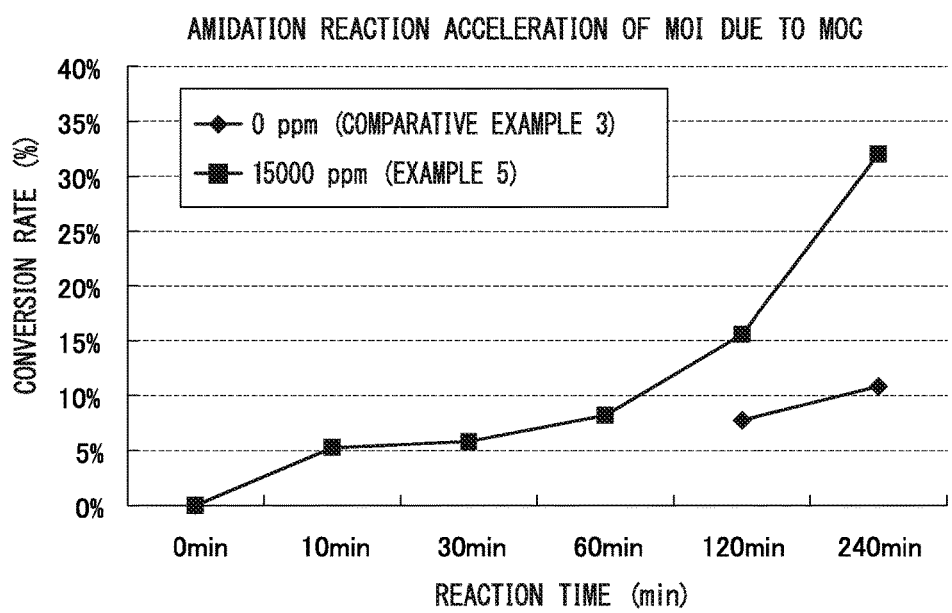
FIG. 3 is a graph showing results of Example 5 and Comparative Example 3 in which an amidation reaction of MOI is performed (change in the conversion ratio of an isocyanate group of MOI to amide with time (amidation rate)).

The time point when MOI was added was set as 0 time in the reaction described above, the reaction solution was sampled at respective time points when elapsed times (reaction times) from 0 time were 0 minute, 10 minutes, 30 minutes, 60 minutes, 120 minutes, and 240 minutes, LC analysis was performed, and the conversion rate thereof (rate of MOI, in which an isocyanate group was converted into amide, from used MOI) was measured. The conversion rate was acquired using the same formula as in Example 1. The results are listed in Table 2 and shown in FIG. 3.

Comparative Example 3

The amidation reaction was performed and the conversion rate was measured in the same manner as in Example 5 except that MOC was not added. The results are listed in Table 2 and shown in FIG. 3.

TABLE 2

| | Amount of MOC | 0 min | 10 min | 30 min | 60 min | 120 min | 240 min |
|---|---|---|---|---|---|---|---|
| Comparative Example 3 | 0 ppm | 0.0% | | | | 7.8% | 10.9% |
| Example 5 | 15000 ppm | 0.0% | 5.3% | 5.8% | 8.2% | 15.6% | 32.0% |

From the above-described results, it was confirmed that MOC functioned as a reaction accelerator in the reaction of isocyanate with carboxylic acid (amidation reaction).

Comparison of Effects of Accelerating Urethanization Reaction Depending on Kinds of Reaction Accelerators to be Added Comparative Example 4

Figure 4:
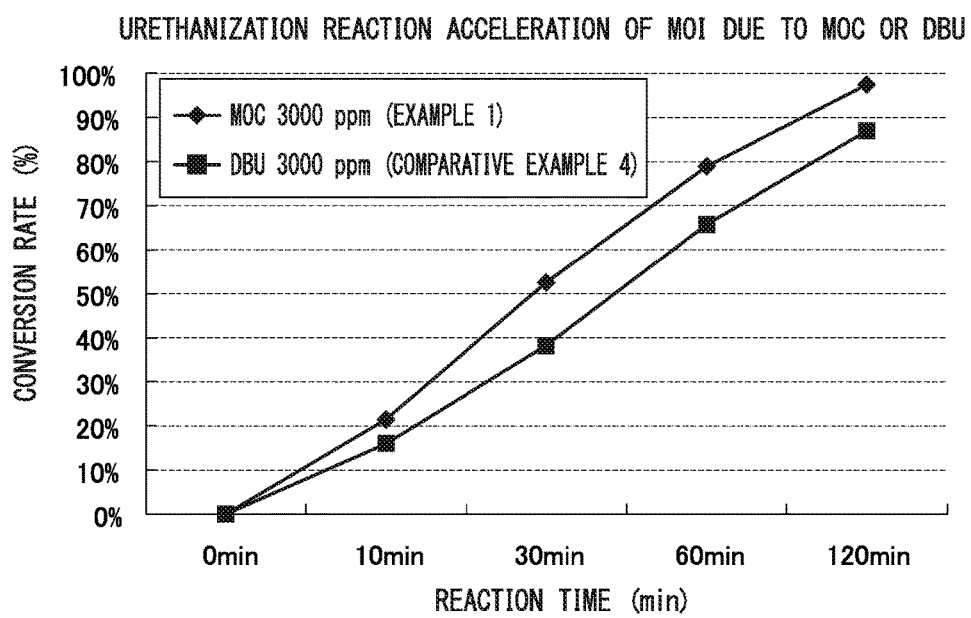
FIG. 4 is a graph showing results of Example 1 and Comparative Example 4 in which a urethanization reaction of MOI is performed (change in the conversion ratio of an isocyanate group of MOI to urethane with time (urethanization rate)).

The urethanization reaction was performed and the conversion rate was measured in the same manner as in Example 1 except that 0.02 g (corresponding to 3000 ppm with respect to MOI) of 1,8-diazabicyclo(5,4,0)undecene (hereinafter, referred to as "DBU," manufactured by Tokyo Chemical Industry Co., Ltd.) in place of MOC. The results are listed in Table 3 and shown in FIG. 4 together with the results of Example 1.

TABLE 3

| | Reaction accelerator | 0 min | 10 min | 30 min | 60 min | 120 min |
|---|---|---|---|---|---|---|
| Example 1 | MOC 3000 ppm | 0.0% | 21.5% | 52.5% | 78.9% | 97.4% |
| Comparative Example 4 | DBU 3000 ppm | 0.0% | 16.0% | 38.2% | 65.8% | 86.9% |

From the above-described results, it is understood that the reaction accelerator of the invention of the present application had excellent reaction acceleration effects in the urethanization reaction compared to an amine-based catalyst.

Difference in Yield Between MOI+MOC System and AOI+MOC System

Example 6

The urethanization reaction was performed in the same manner as in Example 2 except that the reaction was continuously carried out for 1 hour without performing sampling on the reaction solution in the middle of the reaction.

When the reaction solution was LC-analyzed after the reaction, the ratio of a urethane compound having a methacryloyloxy ethyl group to a urethane compound which was generated by the reaction was 100% by mass (ratio of urethane having an acryloyloxy ethyl group was 0%).

Example 7

The urethanization reaction was performed in the same manner as in Example 4 except that the reaction was continuously carried out for 1 hour without performing sampling on the reaction solution in the middle of the reaction.

When the reaction solution was LC-analyzed after the reaction, the ratio of the amount of a urethane compound having a acryloyloxy ethyl group to that of a urethane compound generated by the reaction was 98.8% by mass and 1.2% by mass of a urethane compound having a methacryloyloxy ethyl group was contained. It is considered that this is because MOC used as the reaction accelerator was changed to MOI in the reaction solution and the MOI was reacted with n-butanol.

Effects of Accelerating Radical Polymerization Reaction of Ethylenically Unsaturated Group Due to Reaction Accelerator Reference Example I 5.00 g of MOI (Karenz MOI (registered trademark), manufactured by Showa Denko K.K.) was redistilled and a contained polymerization inhibitor (BHT) was removed. 0.500 g (corresponding to 10000 ppm with respect to MOI) of MOC was added to distilled MOI, a composition obtained by mixing MOC with MOI was purged with nitrogen, and the resultant was heated at 100° C. When the temperature was observed, it was recognized that the temperature was increased at a time point when 20 minutes have elapsed from the time point of addition of MOC, and therefore the start of the reaction of a methacryloyl group (radical polymerization reaction) was confirmed.

Reference Example II

The same operation as in Reference Example 1 was performed except that MOC was not added. When the temperature was observed, it was recognized that the temperature was increased at a time point when 264 minutes have elapsed, and therefore the start of the reaction of a methacryloyl group (radical polymerization reaction) was confirmed.

From the results of Reference Examples I and II, it is confirmed that MOC exhibits not only an effect of accelerating the reaction of an isocyanate group in an isocyanate compound which includes a (meth)acryloyl group but also an effect of accelerating a radical reaction of a (meth) acryloyl group.

However, in Reference Example I, it was confirmed that the radical reaction was started at a time point when 20 minutes were elapsed, which is significantly shorter than that of Reference Example II in spite of the condition in which the heating was performed without adding a radical polymerization initiator (that is, the condition was used which was not a normal photocuring reaction which was carried out by adding a photopolymerization initiator and performing UV irradiation). The result may be considered to be an unpreferable state depending on the purpose of the application or an experimental operation because of storage stability thereof and from the following viewpoints.

In the present invention, since the isocyanate compound having a (meth)acryloyl group includes two functional points of an isocyanate group and a (meth)acryloyl group, it is preferable to produce a cured product by performing two stages of reactions in which the isocyanate group is reacted through heat in advance (first stage) and then the (meth) acryloyl group was reacted through light (second stage). However, when the amount of the polymerization accelerator of the invention of the present application is large, the second-stage reaction may be unexpectedly promoted during the first-stage reaction.

From the above-described background, the amount of the polymerization accelerator of the invention of the present application which is used in a reaction of a bifunctional monomer such as an isocyanate compound including a (meth)acryloyl group is preferably in a range of 5 ppm by mass to 8000 ppm by mass and is more preferably in a range of 5 ppm by mass to 2000 ppm by mass with respect to the amount of the bifunctional monomer.

Example 8

6.72 g (0.04 mol) of hexamethylene diisocyanate (HDI, manufactured by Kanto Kagaku), 0.07 g (corresponding to 10417 ppm with respect to HDI) of MOC, 50 mL of toluene and 0.1 g of BHT were added to a 100 mL three-neck flask and the mixture was stirred and mixed. The obtained mixture was heated to 60° C., 17.8 g of n-butanol was further added to the system, and a reaction of HDI with n-butanol (urethanization reaction) was carried out. During the reaction, the temperature of the reaction solution was held at 60° C.

Figure 5:
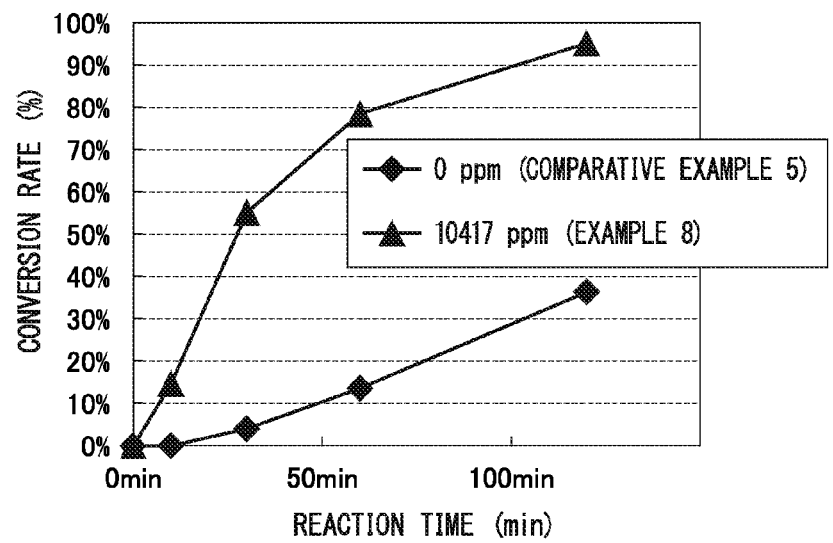
FIG. 5 is a graph showing results of Example 8 and Comparative Example 5 in which a urethanization reaction of HDI is performed (change in the conversion ratio of an isocyanate group of HDI to urethane with time (urethanization rate)).

The time point when n-butanol was added was set as 0 time in the reaction described above, the reaction solution was sampled at respective time points when elapsed times (reaction times) from 0 time were 0 minute, 10 minutes, 30 minutes, 60 minutes, and 120 minutes, LC analysis was performed, and the conversion rate (rate of HDI in which an isocyanate group was converted into urethane from used HDI) was measured. The conversion rate was acquired by the same formula as that in Example 1. The results are listed in Table 4 and shown in FIG. 5.

Comparative Example 5

Figure 8:
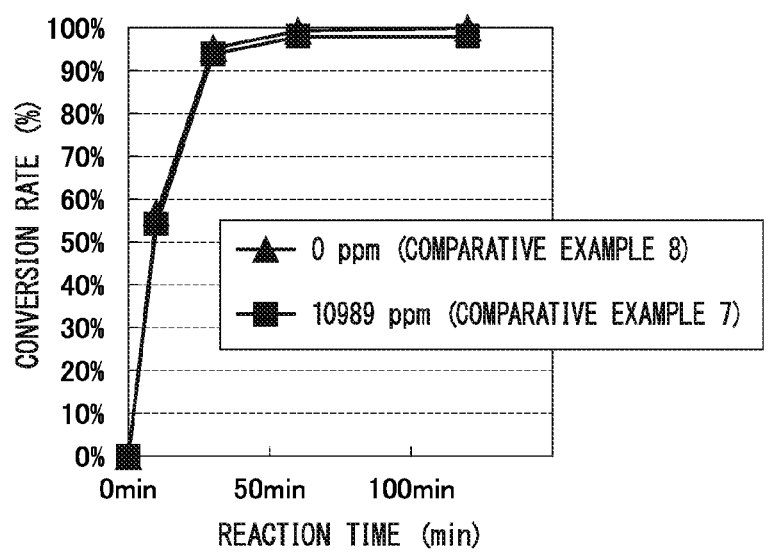
FIG. 8 is a graph showing results of Comparative Examples 7 and 8 in which a urethanization reaction of MDI is performed (change in the conversion ratio of an isocyanate group of MDI to urethane with time (urethanization rate)).

The urethanization reaction was performed and the conversion rate was measured in the same manner as in Example 8 except that MOC was not added. The results are listed in Table 4 and shown in FIG. 5.

converted into urethane from used MDI) was measured in the same manner as in Example 8 except that HDI was changed to 10.01 g (0.04 mol) (according to this, the amount of MOC to be used corresponds to 10989 ppm with respect to MDI) of diphenylmethane diisocyanate (MDI, manufactured by Tokyo Chemical Industry Co., Ltd.) and the heating temperature was changed from 60° C. to 30° C. The results are listed in Table 4 and shown in FIG. 8.

Comparative Example 8

The urethanization reaction was performed and the conversion rate was measured in the same manner as in Example 7 except that MOC was not added. The results are listed in Table 4 and shown in FIG. 8.

From the results of Comparative Examples 7 and 8, an effect of adding the reaction accelerator of the present invention was barely found in the compound in which an isocyanate group was bonded to an aromatic ring such as MDI. The reason for this is considered that the urethanization reaction of the compound in which an isocyanate group is bonded to an aromatic ring is sufficiently rapidly promoted, even under the condition in which the reaction accelerator of the present invention does not exist.

TABLE 4

| | Isocyanate compound | Amount of MOC | 0 min | 10 min | 30 min | 60 min | 120 min | 180 min | 240 min | 360 min | 1440 min |
|---|---|---|---|---|---|---|---|---|---|---|---|
| Comparative Example 5 | HDI | 0 ppm | 0.00% | 0.00% | 4.00% | 13.56% | 36.34% | | 70.47% | 86.50% | |
| Example 8 | | 10417 ppm | 0.00% | 14.73% | 55.10% | 78.46% | 95.19% | | | | |
| Comparative Example 6 | IPDI (primary) | 0 ppm | 0.00% | 9.2% | 29.9% | 49.3% | 70.8% | 81.8% | 89.1% | | 100.0% |
| Example 9 | | 10675 ppm | 0.0% | 100.0% | 100.0% | 100.0% | 100.0% | | | | |
| Comparative Example 6 | IPDI (secondary) | 0 ppm | 0.00% | 0.48% | 1.76% | 4.83% | 13.14% | 22.03% | 30.02% | | 89.66% |
| Example 9 | | 10675 ppm | 0.00% | 46.83% | 92.40% | 99.95% | 100.00% | | | | |
| Comparative Example 8 | MDI | 0 ppm | 0.00% | 56.82% | 95.29% | 99.27% | 100.00% | 100.00% | | | |
| Comparative Example 7 | | 10989 ppm | 0.00% | 54.16% | 93.82% | 97.92% | 97.94% | 97.87% | | | |

Example 9

Figure 6:
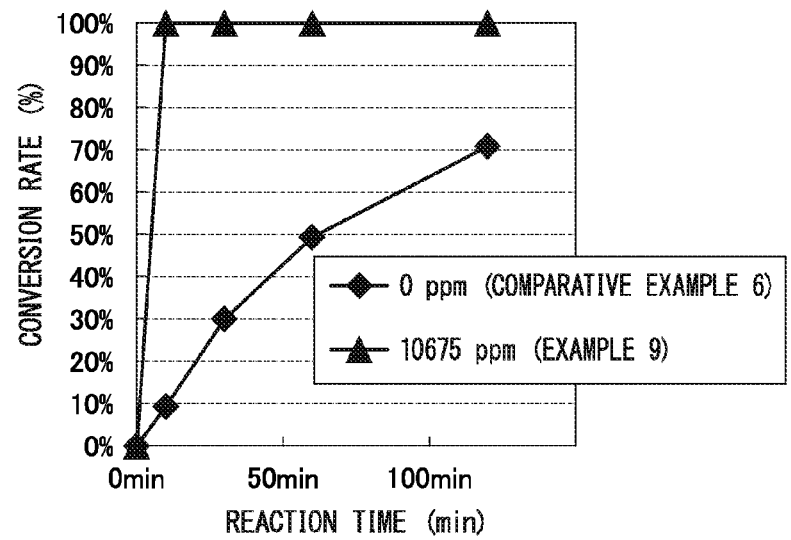
FIG. 6 is a graph showing results of Example 9 and Comparative Example 6 in which a urethanization reaction of IPDI is performed (change in the conversion ratio of a primary isocyanate group of IPDI to urethane with time (urethanization rate)).
Figure 7:
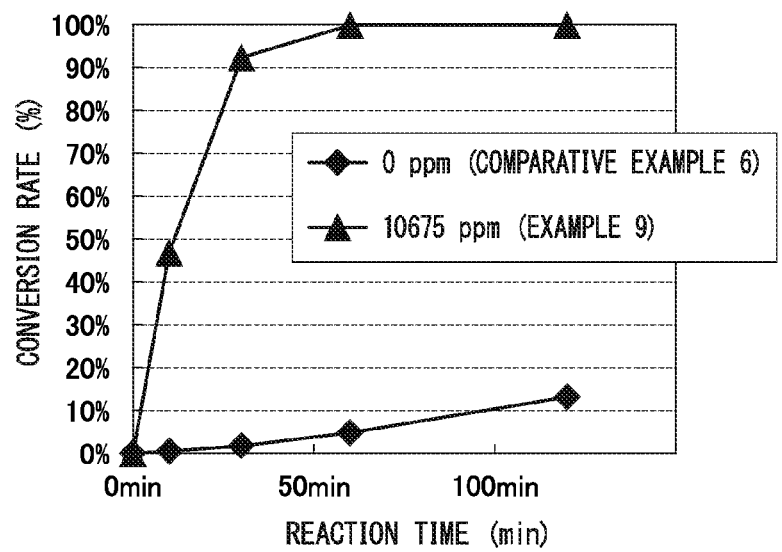
FIG. 7 is a graph showing results of Example 9 and Comparative Example 6 in which a urethanization reaction of IPDI is performed (change in the conversion ratio of a secondary isocyanate group of IPDI to urethane with time (urethanization rate)).

The urethanization reaction was performed and the conversion rate (rate of IPDI in which an isocyanate group was converted into urethane from used IPDI) was measured in the same manner as in Example 8 except that HDI was changed to 8.89 g (0.04 mol) (according to this, the amount of MOC to be used corresponds to 10675 ppm with respect to IPDI) of isophorone diisocyanate (IPDI, manufactured by Tokyo Chemical Industry Co., Ltd.). Further, the conversion rates of a primary isocyanate group and a secondary isocyanate group of IPDI were respectively measured. The results are listed in Table 4 and shown in FIGS. 6 and 7.

Comparative Example 6

The urethanization reaction was performed and the conversion rate was measured in the same manner as in Example 9 except that MOC was not added. The results are listed in Table 4 and shown in FIGS. 6 and 7.

Comparative Example 7

The urethanization reaction was performed and the conversion rate (rate of MDI in which an isocyanate group was

The invention claimed is:

1. A reaction accelerator, wherein
   the reaction accelerator is used in a reaction of a compound comprising an isocyanate group in a molecule, in which the isocyanate group is not directly bonded to an aromatic ring, with a compound including an active hydrogen-containing group, and
   the reaction accelerator is a compound including a halogenated carbamoyl group and a (meth)acryloyl group.

2. The reaction accelerator according to claim 1, wherein the reaction is a reaction that generates a urethane compound, a thiourethane compound, an amide compound or a urea compound.

3. The reaction accelerator according to claim 1, wherein the compound comprising an isocyanate group that is not directly bonded to an aromatic ring in a molecule is at least one selected from a group consisting of hexamethylene diisocyanate, trimethyl hexamethylene diisocyanate, lysine diisocyanate, norbornane diisocyanate, trans-cyclohexane-1,4-diisocyanate, isophorone diisocyanate, bis(isocyanate methyl) cyclohexane, dicyclohexylmethane diisocyanate, dimer acid diisocyanate, m-xylene diisocyanate, m-tetramethylxylene diisocyanate, other diisocyanate compounds represented by the general formula OCN—R—NCO (R represents a divalent aliphatic residue having 1 to 20 carbon atoms), methacroyl isocyanate, 3-isopropenyl-α,α-dimethylbenzyl isocyanate, 3-isocyanatepropyl trimethoxysilane, methacryloyloxyethyl isocyanate, acryloyloxyethyl isocyanate, 1,1-(bisacryloyloxymethyl) ethyl isocyanate, methacryloyloxyethoxyethyl isocyanate, acryloyloxyethoxyethyl isocyanate, and other monoisocyanate compounds represented by the general formula R"—NCO (R" represents a monovalent aliphatic residue having 1 to 20 carbon atoms).

4. The reaction accelerator according to claim 1, wherein the active hydrogen-containing group is a hydroxyl group, a mercapto group, a carbonyl group, or an amino group.

5. The reaction accelerator according to claim 1, wherein the accelerator is a compound represented by the following general formula (I-1) or (I-2)

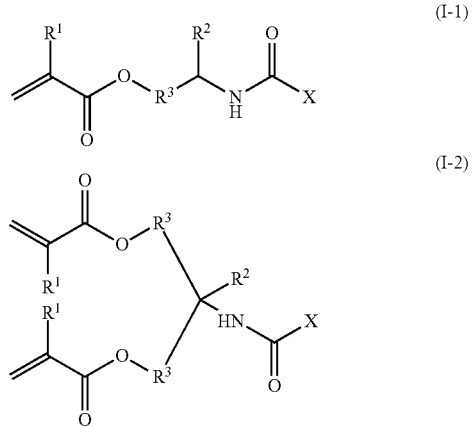

wherein, in the formulae, $R^1$ and $R^2$ each independently represent a hydrogen atom or a methyl group, $R^3$ represents an alkylene group which may include a substituent and has 1 to 10 carbon atoms or a group formed by substituting a single bond between carbon atoms of the alkylene group with a bond selected from a group consisting of an ether bond, an ester bond and a phenylene bond, X represents a fluorine atom, a chlorine atom, a bromine atom or an iodine atom, and two $R^1$'s in the formula (I-2) may be the same as or different from each other and two $R^3$'s may be the same as or different from each other.

6. A production method comprising:
reacting a compound including an isocyanate group that is not directly bonded to an aromatic ring in a molecule with a compound including an active hydrogen-containing group to produce a urethane compound, a thiourethane compound, an amide compound or a urea compound,
wherein the reaction is performed in the presence of the reaction accelerator according to claim 1.

7. The reaction accelerator according to claim 2, wherein the compound comprising an isocyanate group that is not directly bonded to an aromatic ring in a molecule is at least one selected from a group consisting of hexamethylene diisocyanate, trimethyl hexamethylene diisocyanate, lysine diisocyanate, norbornane diisocyanate, trans-cyclohexane-1,4-diisocyanate, isophorone diisocyanate, bis(isocyanate methyl) cyclohexane, dicyclohexylmethane diisocyanate, dimer acid diisocyanate, m-xylene diisocyanate, m-tetramethylxylene diisocyanate, other diisocyanate compounds represented by the general formula OCN—R—NCO (R represents a divalent aliphatic residue having 1 to 20 carbon atoms), methacroyl isocyanate, 3-isopropenyl-α,α-dimethylbenzyl isocyanate, 3-isocyanatepropyl trimethoxysilane, methacryloyloxyethyl isocyanate, acryloyloxyethyl isocyanate, 1,1-(bisacryloyloxymethyl) ethyl isocyanate, methacryloyloxyethoxyethyl isocyanate, acryloyloxyethoxyethyl isocyanate, and other monoisocyanate compounds represented by the general formula R"—NCO (R" represents a monovalent aliphatic residue having 1 to 20 carbon atoms).

* * * * *

UNITED STATES PATENT AND TRADEMARK OFFICE
CERTIFICATE OF CORRECTION

Page 1 of 1

PATENT NO. : 9,656,952 B2
APPLICATION NO. : 14/906759
DATED : May 23, 2017
INVENTOR(S) : Katsutoshi Ono and Tomomitsu Kato It is certified that error appears in the above-identified patent and that said Letters Patent is hereby corrected as shown below:

In the Specification

Column 2, Line 61 and In the Claims, Column 23, Line 12, change "carbonyl" to --carboxyl--.

Signed and Sealed this
Fourteenth Day of May, 2019

Andrei Iancu
*Director of the United States Patent and Trademark Office*